United States Patent
Endo et al.

(10) Patent No.: US 9,410,929 B2
(45) Date of Patent: Aug. 9, 2016

(54) INSPECTION DEVICE AND INSPECTION METHOD

(71) Applicant: Hitachi, Ltd., Chiyoda-ku, Tokyo (JP)

(72) Inventors: Hisashi Endo, Tokyo (JP); Soshi Narishige, Tokyo (JP); Mitsuteru Inoue, Toyohashi (JP); Hiroyuki Takagi, Toyohashi (JP)

(73) Assignee: Hitachi, Ltd., Tokyo (JP)

( * ) Notice: Subject to any disclaimer, the term of this patent is extended or adjusted under 35 U.S.C. 154(b) by 78 days.

(21) Appl. No.: 14/177,965

(22) Filed: Feb. 11, 2014

(65) Prior Publication Data

US 2014/0225606 A1     Aug. 14, 2014

(30) Foreign Application Priority Data

Feb. 13, 2013   (JP) ................. 2013-025703

(51) Int. Cl.
*G01N 27/82*   (2006.01)
*G01N 27/72*   (2006.01)
*H01J 37/26*   (2006.01)
*G01N 21/21*   (2006.01)
(Continued)

(52) U.S. Cl.
CPC ............ *G01N 27/82* (2013.01); *G01R 33/0322* (2013.01); *G01N 21/21* (2013.01); *G01N 21/8806* (2013.01); *G01N 27/72* (2013.01); *G01R 33/032* (2013.01)

(58) Field of Classification Search
USPC ............. 324/260, 240, 238, 228, 244, 244.1, 324/529, 754.29, 207.21, 207.22, 219, 237, 324/216, 213, 226, 200, 214, 220; 356/237.1, 237.2, 237.3, 369, 445, 456
See application file for complete search history.

(56) References Cited

U.S. PATENT DOCUMENTS 5,053,704 A    10/1991   Fitzpatrick
5,949,901 A     9/1999   Nichani et al.
(Continued)

FOREIGN PATENT DOCUMENTS

IN   WO 2012049538 A1 *  4/2012 ............. G01N 21/21
JP       62-110139 A       5/1987
(Continued)

OTHER PUBLICATIONS

Hu et al, "Optical system design for crack inspections using magneto-optical imaging", Optical Metrology and Inspection for Industrial Applications, Proc. of SPIE, vol. 7855, 2010.*
(Continued)

*Primary Examiner* — Jennifer Wecker
(74) *Attorney, Agent, or Firm* — Crowell & Moring LLP

(57) ABSTRACT

Provided are an inspection device and an inspection method capable of achieving improved magnetic field sensitivity by using a magnetic thin film of a small film thickness. A light-emitting unit 1 emits light of a first wavelength for acquiring magnetic field inspection information and a second wavelength for acquiring inspection object surface information. A selection unit 6 selects information from an inspection object 4 and information from a magnetophotonic crystal film 3 acquired by light irradiation performed by an irradiation unit 2. An image generation unit 9 generates image data based on the magnetic field inspection information acquired with the first wavelength and the inspection object surface information acquired with the second wavelength selected by the selection unit. Each of the generated image data is displayed on a display unit 10.

12 Claims, 11 Drawing Sheets

(51) Int. Cl.
*G01R 33/032* (2006.01)
*G01N 21/88* (2006.01)

(56) References Cited

U.S. PATENT DOCUMENTS

| | | | |
|---|---|---|---|
| 7,501,816 B2 | 3/2009 | Higuchi | |
| 2006/0146328 A1 | 7/2006 | Decitre et al. | |
| 2012/0092484 A1* | 4/2012 | Taniguchi | G01N 21/956 |
| | | | 348/87 |
| 2012/0092657 A1* | 4/2012 | Shibata | G01N 21/95607 |
| | | | 356/237.4 |
| 2013/0277553 A1* | 10/2013 | Otani | G01N 21/8806 |
| | | | 250/307 |
| 2014/0176698 A1* | 6/2014 | Banerjee | G01N 21/21 |
| | | | 348/92 |

FOREIGN PATENT DOCUMENTS

| | | |
|---|---|---|
| JP | 6-118060 A | 4/1994 |
| JP | 6-273349 A | 9/1994 |
| JP | 2006-215018 A | 8/2006 |
| WO | WO 2012/049538 A1 | 4/2012 |

OTHER PUBLICATIONS

European Search Report dated Jun. 2, 2015 (10 pages).

Qingying et al. "Optical system design for crack inspection using magneto-optical imaging" Optical Metrology and Inspection for Industrial Applications, Proceedings of SPIE, Nov. 3, 2010, eight pages, vol. 7855, Quest Integrated Inc., Kent, WA, XP055190382.

Wincheski et al. "Imaging Flaws in Thin Metal Plates using a Magneto-Optic Device" Review of Progress in Quantitative Nondestructive Evaluation, Jan. 1, 1992, pp. 871-878, vol. 11, NASA Langley Research Center, Hampton, Virginia, XP055190658.

Klank et al. "Characterization and optimization of magnetic garnet films for magneto-optical visualization of magnetic field distributions" NDT&E International, Science Direct, Sep. 2, 2003, pp. 375-381, vol. 36, No. 6, Department of Physics, University of Osnabruick et al., Osnabruick, Germany, XP004434265.

R. Hashimoto et al., "Fundamental study of magneto-optic imaging with polycrystalline iron garnet sputtered films for high spatial resolution non-destructive inspection," MAG 12-89, (Sep. 24, 2012), pp. 39-42 with English-language abstract (six (6) pages).

Japanese-language Office Action issued in counterpart Japanese Application No. 2013-025703 dated Apr. 26, 2016 (six (6) pages).

\* cited by examiner

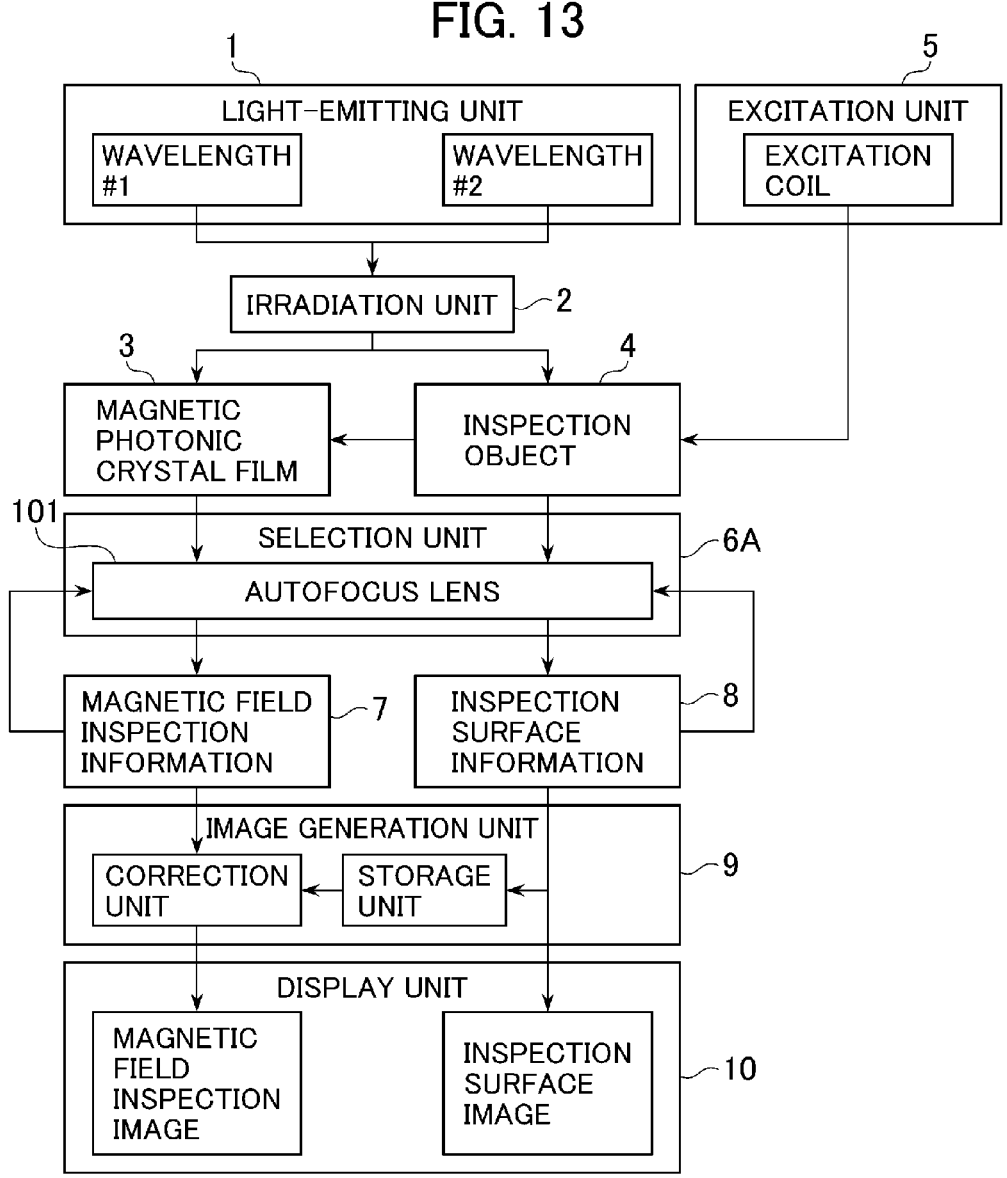

INSPECTION DEVICE AND INSPECTION METHOD

BACKGROUND OF THE INVENTION

1. Field of the Invention

The present invention relates to an inspection device and an inspection method for evaluating characteristic changes (flaws, material property changes, etc.) in an inspection object, and in particular, to an inspection device and an inspection method suitable for the use of a magnetic inspection probe.

2. Description of the Related Art

Nondestructive testing methods employ a magnetic field. In such nondestructive testing methods, an excitation coil is energized or permanent magnets are used to generate a magnetic field. The thus-generated magnetic field is applied to a metallic material as the inspection object and then a difference in the magnetic field distribution, which is caused by flaws and/or material property changes, is detected by use of a magnetic sensor. The leakage magnetic flux method and the eddy current flaw detection method (eddy current testing method) are well-known as representative techniques of the nondestructive testing method employing a magnetic field. The leakage magnetic flux method generally employs a DC magnetic field (with no temporal change in the magnetic field intensity) or low-frequency excitation. The inspection object is infiltrated with magnetic flux therein. Magnetic flux leaking out from a part of the inspection object metal (i.e., the metallic material as the inspection object) in the vicinity of a flaw is detected by use of a magnetic sensor. In the eddy current flaw detection method, magnetic flux having a change in the magnetic flux intensity is generated by supplying a time-varying electric current (with a temporal change in the electric current value) to an excitation coil of an eddy current probe. Eddy current is caused by bringing the eddy current probe closer to the metal object (inspection object) and changes in the eddy current are detected as detection signals by a magnetic sensor.

These methods employ a magnetic sensor such as a coil or a Hall effect sensor for the detection of the magnetic field. Therefore, mechanical scanning of the probe becomes necessary for thoroughly inspecting the surface of the inspection object. In order to reduce the mechanical scanning, there has been proposed a technique for instantaneously imaging the detection signal by using an array sensor having an array of magnetic sensors. However, the spatial resolution of the obtained image varies depending on the size of the coil or Hall effect sensor used as the magnetic sensor.

Meanwhile, to further increase the resolution, a magnetic field inspection method introducing the magnetic field detection by use of light (which is called "magneto-optical effect") is being developed. For example, there is a known probe (see JP-2006-215018-A, for example) in which the magnetic sensor is downsized by using a magnetic thin film capable of detecting the magnetic field by use of the magneto-optical effect. Further, there is a known device (see U.S. Pat. No. 5,053,704, for example) that employs a similar principle and acquires inspection signals as images by shooting a magnetic thin film with a camera. In either technique, a magnetic thin film is arranged over the inspection object surface, the magnetic thin film is irradiated with light, and the magnetic field is detected and evaluated by receiving reflected light from the magnetic thin film as response light.

The magneto-optical effect employed for these techniques is a phenomenon in which the polarization angle of light applied to magnetic material changes (rotates) depending on the status of magnetization of the magnetic material, which is well-known as the Kerr effect (for the reflected light from the object material) or the Faraday effect (for the transmitted light emerging from the object material). The amount of the rotation of the polarization angle corresponds to the sensitivity to the magnetic field, which increases with the increase in the distance of passage of the light through the object material. For this reason, the method using the transmitted light emerging from the object material (i.e., the Faraday effect) is generally employed for the nondestructive testing needing high sensitivity to the magnetic field. In this method, a reflective plate is arranged on one side of the employed magnetic thin film and the light to be used as the magnetic field information is received via an analyzer.

SUMMARY OF THE INVENTION

However, in the technique described in JP-2006-215018-A, a sensor unit is configured by thickening the magnetic thin film in order to achieve high sensitivity to the magnetic field and the shape of the sensor unit is rounded so as to allow more magnetic flux to pass through the magnetic thin film. On the other hand, when the so-called "lift-off" (increase in the distance between the sensor and the inspection object) takes place, noise tends to occur due to the thickness of the sensor unit.

The technique described in U.S. Pat. No. 5,053,704 is capable of gathering the inspection data as images; however, a reflective plate made of metal (e.g. aluminum) has to be arranged on one side of the magnetic thin film so that the reflected light can be captured by the camera. If an electric conductor such as the aluminum plate is used in the eddy current-based measurement method, eddy current occurs in the electric conductor and there is apprehension that the eddy current in the electric conductor can act as noise against the phenomenon deriving from the object of the measurement (e.g. flaw), as described also in JP-2006-215018-A. Further, the noise due to the lift-off tends to occur also in this technique since the magnetic thin film is formed to be thick to increase the sensitivity similarly to the technique of JP-2006-215018-A.

It is therefore the primary object of the present invention to provide an inspection device and an inspection method capable of achieving improved magnetic field sensitivity by using a magnetic thin film of a small film thickness.

To achieve the above object, the present invention provides an inspection device for evaluating characteristic changes in an inspection object such as flaws and material property changes by using magnetism, wherein the inspection device employs a magnetophotonic crystal film. Specifically, the magnetophotonic crystal film is a film-shaped magnetic field detection element arranged immediately above an inspection object surface of the inspection object in order to detect a magnetic field generated by an excitation unit. The inspection device comprises: a light-emitting unit which emits light of a first wavelength for acquiring magnetic field inspection information and a second wavelength for acquiring inspection object surface information; an irradiation unit which irradiates the inspection object with the light from the light-emitting unit; a selection unit which selects information from the inspection object and information from the magnetophotonic crystal film acquired by the light irradiation by the irradiation unit as the inspection object surface information and the magnetic field inspection information; an image generation unit which generates image data based on the magnetic field inspection information acquired with the first wavelength and the inspection object surface information acquired with the second wavelength selected by the selection unit; and a display unit which displays the image data generated by the image generation unit.

The present invention also provides an inspection method for evaluating characteristic changes in an inspection object such as flaws and material property changes, wherein the characteristic changes such as flaws and material property changes are detected by a magnetic field inspection while also detecting flaws on the inspection object surface by an optical inspection by performing the following steps: irradiating a magnetophotonic crystal film with light of a first wavelength for acquiring magnetic field inspection information emitted from a light-emitting unit; irradiating the inspection object with light of a second wavelength for acquiring inspection object surface information emitted from the light-emitting unit; generating image data based on the magnetic field inspection information acquired from the magnetophotonic crystal film and the inspection object surface information acquired from the inspection object; and displaying the generated image data.

With the above configuration and method according to the present invention, the magnetic field sensitivity can be improved by using a magnetic thin film of a small film thickness.

EFFECT OF THE INVENTION

In accordance with the present invention, the magnetic field sensitivity can be improved by using a magnetic film of a small film thickness.

BRIEF DESCRIPTION OF THE DRAWINGS

FIG. 12 is a table showing an example of the result of calculation of compensation coefficients.

FIG. 13 is a block diagram showing the overall configuration of an inspection device according to a second embodiment of the present invention.

DESCRIPTION OF THE PREFERRED EMBODIMENTS

First Embodiment

In the following, an inspection device and an inspection method in accordance with a first embodiment of the present invention will be described referring to FIGS. 1-12.

First, the overall configuration of the inspection device according to this embodiment will be explained referring to FIGS. 1-3.

Figure 1:
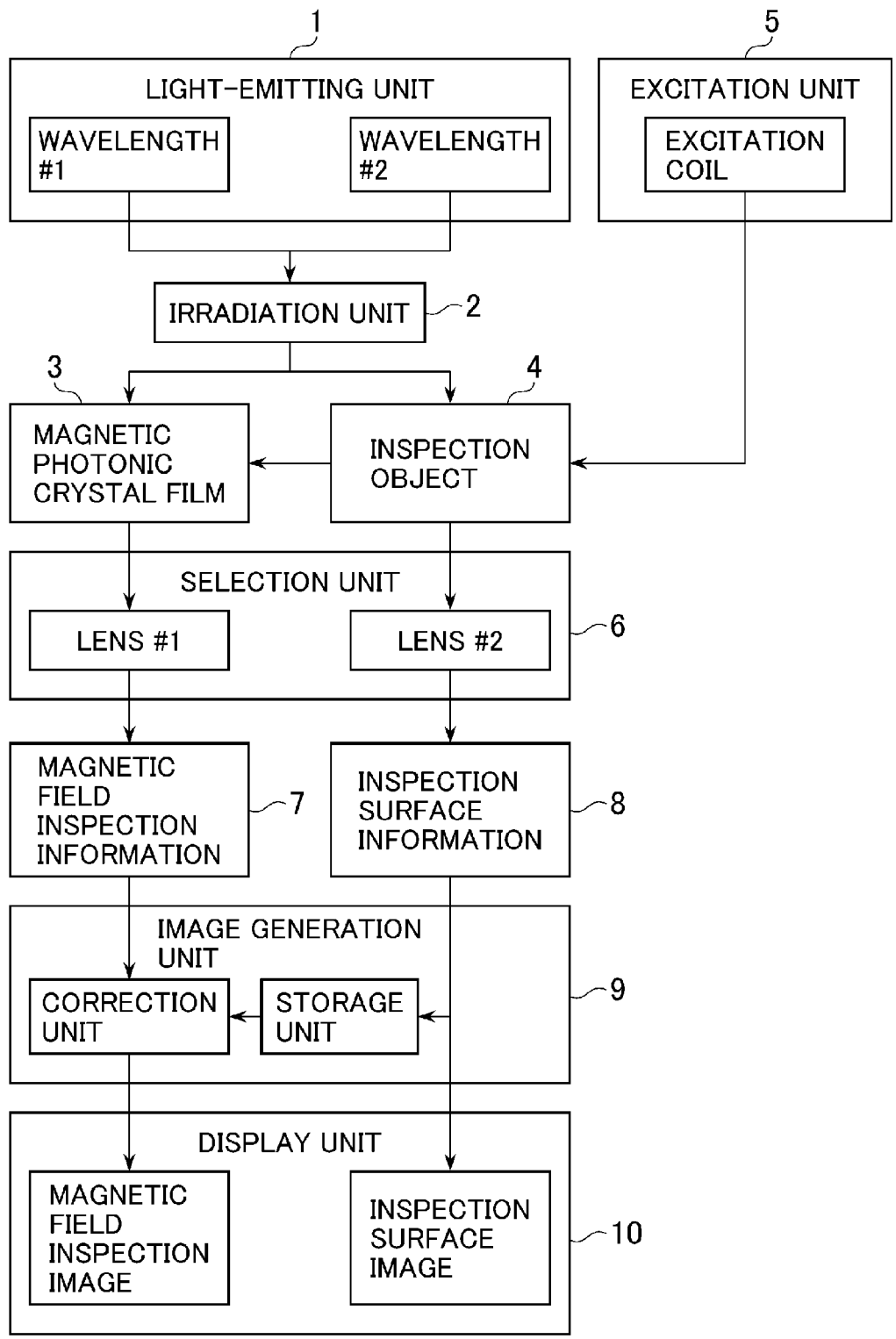
FIG. 1 is a block diagram showing the overall configuration of an inspection device according to a first embodiment of the present invention.
Figure 2:
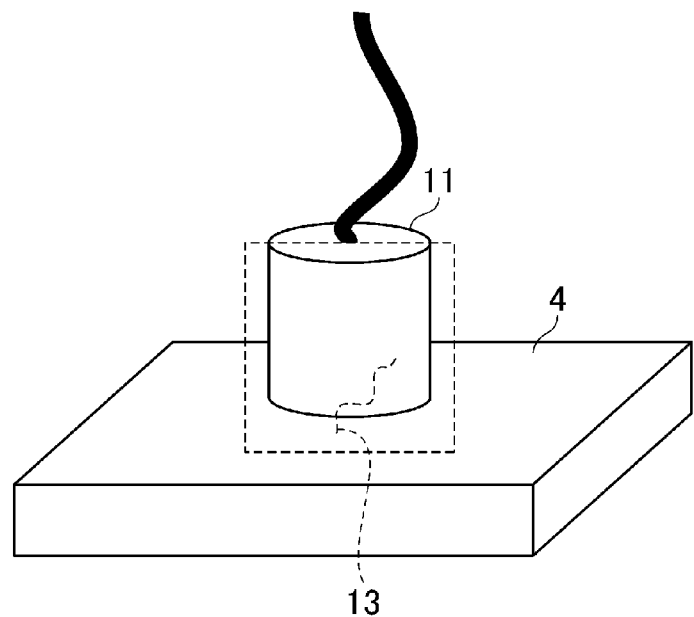
FIG. 2 is a schematic diagram for explaining a crack measurement scheme employed by the inspection device according to the first embodiment of the present invention.

FIG. 1 is a block diagram showing the overall configuration of the inspection device according to the first embodiment of the present invention. FIG. 2 is a schematic diagram for explaining a crack measurement scheme employed by the inspection device according to the first embodiment of the present invention. FIG. 3 is a detailed configuration diagram of a principal part of the inspection device according to the first embodiment of the present invention. In FIGS. 1-3, identical reference characters represent the same component. Incidentally, the example shown in FIGS. 2 and 3 is not intended to restrict this embodiment of the present invention.

In the magnetic field inspection method typified by the leakage magnetic flux method and the eddy current testing method, the inspection object metal (i.e., metallic material as the inspection object) is irradiated with DC or AC magnetic field and a difference in the magnetic field caused by a crack or a change in the material is detected by using a magnetic field detection element. In general, the magnetic field detection element converts the magnetic field information into an electric signal by using a device (detection coil, Hall effect sensor, etc.) that yields an electric output, and necessary information is acquired by processing the electric signal. In the present invention, a magnetic thin film exhibiting the magneto-optical effect is employed as the magnetic field detection element.

A light-emitting unit 1 is capable of emitting light of two wavelengths (wavelength #1, wavelength #2). While the two wavelengths will be explained later, the wavelength #1 is used for the magnetic field inspection (e.g. 540 nm), while the wavelength #2 is used for acquiring optical inspection images (e.g. 630 nm). The light-emitting unit 1 includes a white light source which emits visible light and a wavelength selection unit (spectroscope, interference filter, etc.) which extracts light of prescribed wavelengths. It is also possible to employ light-emitting diodes or laser diodes depending on the values of the wavelengths #1 and #2.

The light emitted from the light-emitting unit 1 is applied by an irradiation unit 2 to an inspection object 4 and a magnetophotonic crystal film 3 which is used as a magnetic thin film arranged over the inspection object 4. The irradiation unit 2 includes a lens, a polarizer for adjusting the light into a linearly-polarized wave, and a mirror such as a half mirror for changing the input/output directions of the light.

An excitation unit 5, including an excitation coil, generates a DC or AC magnetic field and applies the magnetic field to the inspection object 4. When a characteristic change (flaw, material property change, etc.) exists in the inspection object 4, the magnetic field changes around the position of the characteristic change. The change in the magnetic field causes a change in the magnetic field distribution in the magnetophotonic crystal film 3. The change in the magnetic field distribution causes variations in the polarization angle of the light (phenomenon called "Faraday effect") in the magnetophotonic crystal film 3.

A selection unit 6 includes lenses #1 and #2. The lens #1 is used for acquiring magnetic field inspection information 7 from the surface status of the magnetophotonic crystal film 3. The lens #1 forms an image on the surface of the magnetophotonic crystal film 3. The lens #2 is used for acquiring inspection object surface information 8 from the surface status of the inspection object 4. The lens #2 forms an image on the surface of the inspection object 4. It is also possible, instead of using two lenses, to use only one lens and move the lens on the optical axis to make the lens form an image on the surface of the magnetophotonic crystal film 3 and on the surface of the inspection object 4.

The selection unit 6 further includes an analyzer for converting the light into light intensity depending on the polarization angle of the light, a mirror such as a half mirror for changing the input/output directions of the light, and a two-dimensional photoreceptor device such as a CCD camera or a photodiode.

The light after undergoing the Faraday effect is separated by the selection unit 6 into the magnetic field inspection information 7 and the inspection object surface information 8. An image generation unit 9 generates a magnetic field inspection image and an inspection surface image from the data selected by the selection unit 6. The generated images are displayed on a display unit 10 such as the display of a personal computer or a monitor screen.

The image generation unit 9 includes a storage unit for storing the inspection object surface information 8 and a correction unit. The correction unit of the image generation unit 9 corrects the magnetic field inspection information by using the inspection object surface information stored in the storage unit. Details of the correction will be explained later.

Next, the crack measurement scheme employed by the inspection device according to this embodiment will be explained below referring to FIG. 2. FIG. 2 shows an example of the measurement scheme employed for flaw detection.

An inspection probe 11 is set on the inspection object 4. The inspection object 4 is assumed to have a flaw 13. The flaw 13 is detected by the inspection probe 11. The inspection probe 11 includes the light-emitting unit 1, the excitation unit 5, the irradiation unit 2, the magnetophotonic crystal film 3 and the selection unit 6 shown in FIG. 1.

Next, the internal structure of the inspection probe 11 will be explained below referring to FIG. 3.

In order to generate magnetic flux passing through the inspection object 4, the inspection probe 11 includes an excitation coil 16 wound around a magnetic core 15. Magnetic flux 17 is generated by energizing the excitation coil 16 with DC or AC current. The excitation unit 5 shown in FIG. 1 is formed by the magnetic core 15 and the excitation coil 16.

The magnetic flux changes its propagation path when it reaches the vicinity of a crack. For example, when there is leakage magnetic flux leaking out from a crack, the magnetic field is strong at positions almost directly above the crack. By taking advantage of this phenomenon, the crack can be detected with a magnetic sensor installed in the probe.

In this embodiment, the magnetophotonic crystal film 3 exhibiting the magneto-optical effect is employed. The detection of the crack is performed by having the magnetic field distribution copied into the magnetophotonic crystal film 3 and reading out the copied magnetic field distribution by use of light.

The light 19 used for this process is emitted by a light source 1 which is employed as the light-emitting unit. In this example, the light source 1 is equipped with an interference filter and a spectroscope for extracting the two wavelengths.

The irradiation unit 2 shown in FIG. 1 includes a lens 20, a polarizer 21 for adjusting the light into a linearly-polarized wave, and a mirror 22 such as a half mirror for changing the input/output directions of the light. The light from the light source 1 is applied by the irradiation unit 2 to the inspection object 4 and the magnetophotonic crystal film 3 which is used as the magnetic thin film arranged over the inspection object 4. In this example, the lens 20 is movable in the optical axis direction. By the movement of the lens 20, the image of the light source 1 can be formed on either the magnetophotonic crystal film 3 or the inspection object 4, by which the illuminance is increased on the surface of the magnetophotonic crystal film 3 and on the surface of the inspection object 4.

The light irradiating the magnetophotonic crystal film 3 and the inspection object 4 is reflected by the surface of the magnetophotonic crystal film 3 and the surface of the inspection object 4 and the reflected light from each surface is selected by the selection unit. The selection unit 6 shown in FIG. 1 includes the mirror 22 such as a half mirror for changing the input/output directions of the light, a lens 24 for adjusting the focal point, an analyzer 23 for converting the light into light intensity depending on the polarization angle of the light, and a two-dimensional photoreceptor device 25 such as a CCD camera or a photodiode. The light reflected by the magnetophotonic crystal film 3 or the inspection object 4 is received by the photoreceptor device 25.

Information on the Faraday effect occurring in the magnetophotonic crystal film 3 due to a change in the magnetic field distribution (i.e., information on the rotation of the polarization angle) is acquired by the photoreceptor device 25 as the magnetic field inspection information. In this case, the lens 24 moves on its optical axis so as to be provided an image of the magnetophotonic crystal film 3. In order to acquire an image of the surface of the inspection object 4, the lens 24 moves on the optical axis so as to be provided an image of the inspection object 4.

Figure 4:
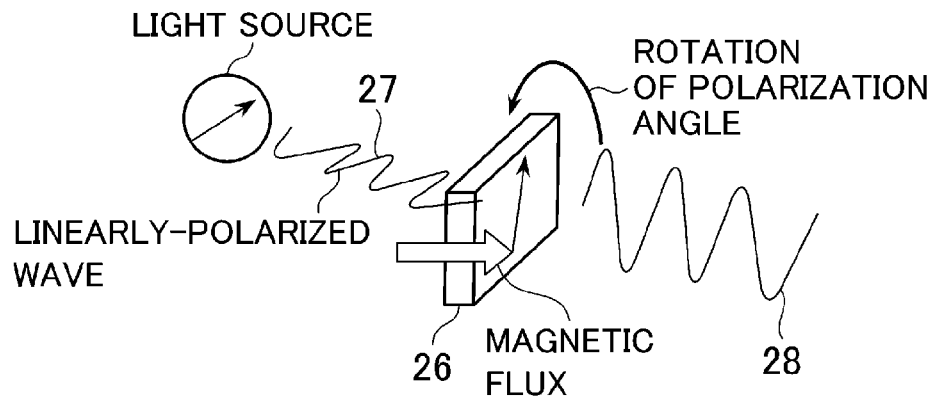
FIG. 4 is a schematic diagram for explaining magneto-optical effect employed for the inspection device according to the first embodiment of the present invention.
Figure 5:
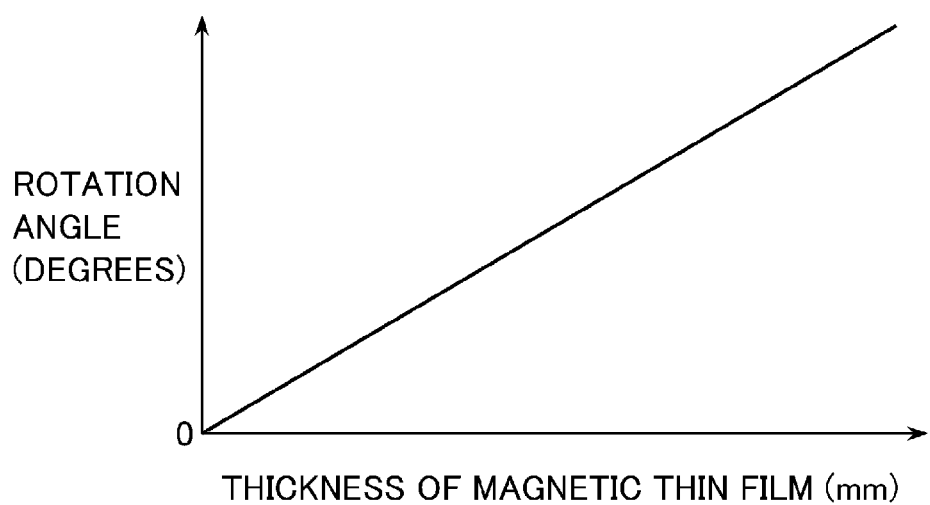
FIG. 5 is a graph for explaining the relationship between film thickness of a magnetic thin film and rotation of the polarization angle in the magneto-optical effect.

Next, the magneto-optical effect will be explained briefly by referring to FIGS. 4 and 5. FIG. 4 is a schematic diagram for explaining the magneto-optical effect employed for the inspection device according to the embodiment of the present invention. FIG. 5 is a graph for explaining the relationship between the film thickness of the magnetic thin film and the rotation of the polarization angle in the magneto-optical effect.

As shown in FIG. 4, when linearly-polarized incident light 27 passes through the magnetic thin film 26 exhibiting the magneto-optical effect, the magnetization of the magnetic thin film 26 changes due to the magnetic field (magnetic flux)

applied to the thin film. As a result, output light 28 having a rotated polarization angle is obtained.

In this case, the rotation of the polarization angle due to the Faraday effect continues longer with the increase in the distance of passage of the light through the magnetic thin film 26. Thus, when the intensity of the magnetic field applied to the magnetic thin film 26 is constant, the rotation of the polarization angle increases with the increase in the film thickness of the magnetic thin film 26. In other words, the sensitivity to the magnetic field intensity increases with the increase in the film thickness of the magnetic thin film 26.

FIG. 5 shows the relationship between the film thickness of the magnetic thin film 26 and the rotation of the polarization angle. The Faraday rotation angle represented by the vertical axis has a tendency to increase with the increase in the film thickness (thickness of the magnetic thin film) represented by the horizontal axis. Therefore, increasing the film thickness is a method commonly used for increasing the sensitivity of the magnetic thin film 26.

Next, the configuration of the magnetic thin film for causing the magneto-optical effect will be explained below referring to FIGS. 6 and 7.

Figure 6:
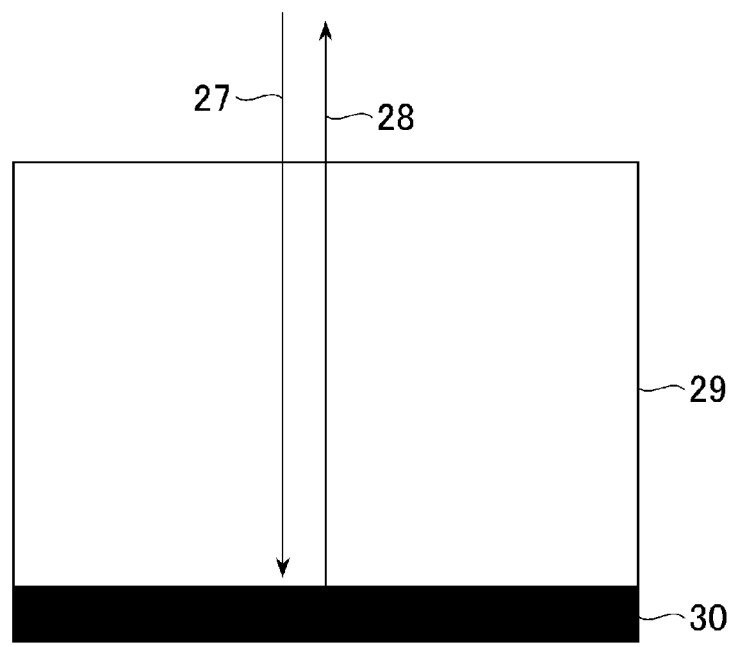
FIG. 6 is a schematic diagram for explaining the configuration of a conventional reflective thin film sensor.

FIG. 6 is a schematic diagram for explaining the configuration of a conventional reflective thin film sensor. FIG. 7 is a schematic diagram for explaining the configuration of a reflective thin film sensor employed for the inspection device according to the embodiment of the present invention.

FIG. 6 shows an example of the structure of a reflective thin film sensor employing the Faraday effect (JP-2006-215018-A, U.S. Pat. No. 5,053,704, etc.).

The reflective thin film sensor includes a magnetic layer 29 exhibiting the Faraday effect and a reflective plate 30 (e.g. aluminum plate) arranged on one side of the magnetic layer 29. The magnetic layer 29 is made of magnetic garnet, for example. Aluminum or the like is vapor-deposited on the magnetic layer 29. By having the incident light 27 enter the magnetic layer 29 from the side opposite to the aluminum layer, the output light 28 as the reflected light can be obtained. Since the rotation of the polarization angle increases with the increase in the film thickness as explained above, the magnetic layer 29 is desired to be thicker.

Figure 7:
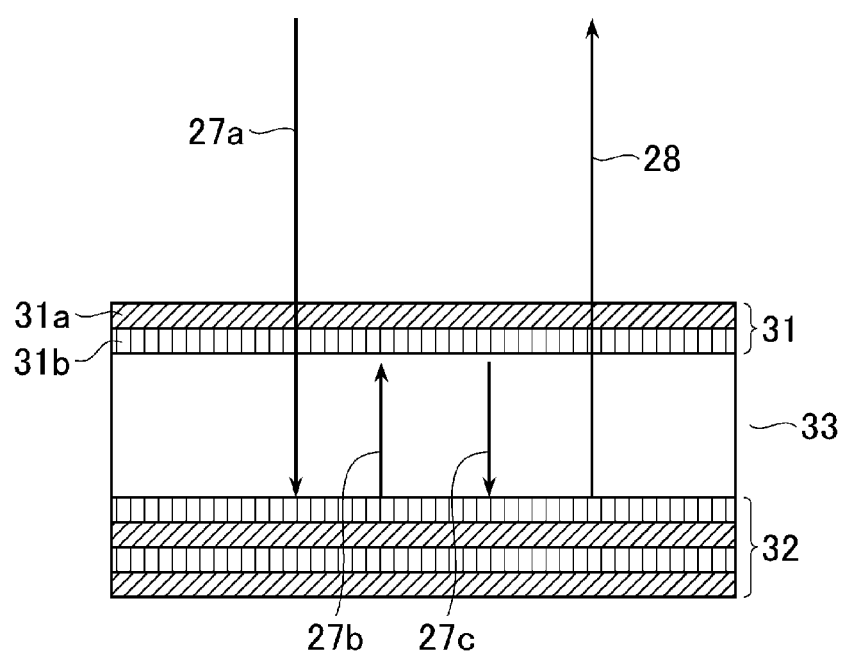
FIG. 7 is a schematic diagram for explaining the configuration of a reflective thin film sensor employed for the inspection device according to the first embodiment of the present invention.

FIG. 7 shows an example of the structure of the reflective thin film sensor employed in this embodiment.

The reflective thin film sensor employed in this embodiment has structure called "micro-cavity", in which a magnetic layer 33 is sandwiched between laminated dielectric mirrors 31 and 32. Such a thin film is called a "magnetophotonic crystal film". A magnetophotonic crystal is an artificial crystal formed by stacking magnetic bodies and dielectric bodies differing in the refractive index (dielectric constant) periodically in sizes around the wavelength of the light. By setting the optical film thickness of the multi-layer film formed of dielectric bodies differing in the refractive index (dielectric multi-layer film) at $d=n\lambda/4$ (d: physical film thickness of each dielectric body, $\lambda$: wavelength of the light, n: refractive index of each dielectric body), there appears a range called a "photonic band gap", where the existence of light in a certain wavelength range is not allowed to the propagating light. This band gap can be set arbitrarily by changing the materials and the structure of the dielectric multi-layer film. The dielectric mirror 31 used in the example of FIG. 7 is formed by stacking up tantalum pentoxide 31a and oxide silicon 31b. The dielectric mirror 32 has structure similar to the dielectric mirror 31. Incidentally, similar effect can be achieved even if the dielectric mirrors 31 and 32 are formed in structure obtained by interchanging the tantalum pentoxide 31a and the oxide silicon 31b.

In this case, the incident light 27a entering the thin film sensor undergoes multiple reflection between the dielectric mirrors 31 and 32. As a result of the multiple reflection, the output light 28 is obtained. This is a phenomenon caused by the so-called "local existence mode". When there exists a magnetic layer 29 that disturbs part of the periodical structure of the dielectric multi-layer film, the light is localized in the part where the periodical structure is disturbed, and light of a particular wavelength is allowed through the photonic band gap (local existence mode). Consequently, reflection like the arrows 27b and 27c (indicating paths of light) in FIG. 7 occurs multiple times and the distance of passage of the light through the magnetic layer 33 increases due to the multiple reflection. This achieves an effect similar to increasing the film thickness of the thin film sensor in the example of FIG. 6. Thus, a great change (rotation) of the polarization angle can be realized even with a small film thickness. In other words, it becomes possible to bring the magnetic field sensing position of the thin film sensor closer to the inspection object.

Next, the effect of "lift-off" and a method for compensating for the effect of the lift-off will be explained below referring to FIGS. 8A-12.

First, the magnetic field intensity when lift-off LO has occurred between the thin film sensor and the inspection object will be explained referring to FIGS. 8A and 8B.

Figure 8A:
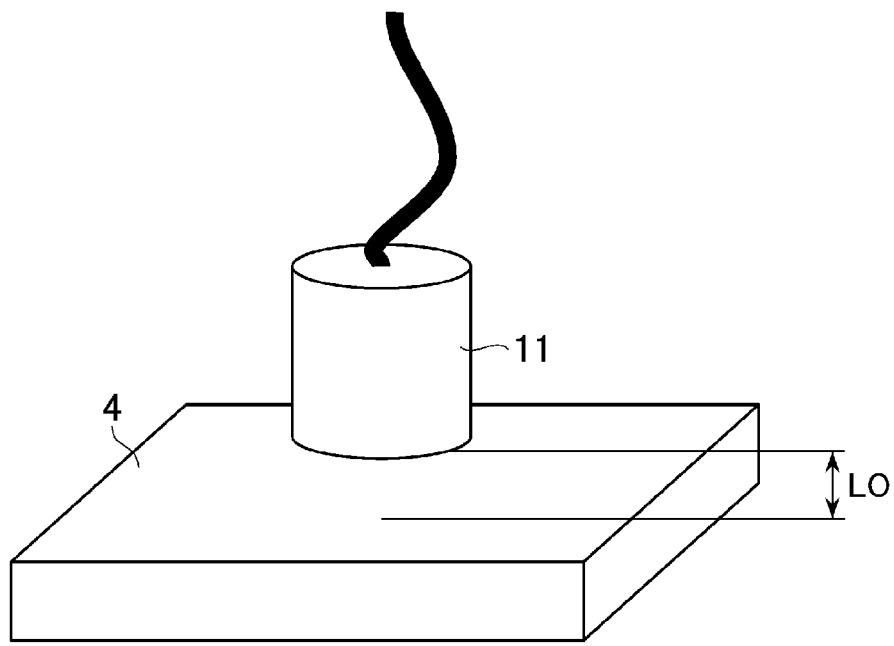
FIGS. 8A and 8B are schematic diagrams for explaining the magnetic field intensity when lift-off LO has occurred between the thin film sensor and the inspection object.
Figure 8B:
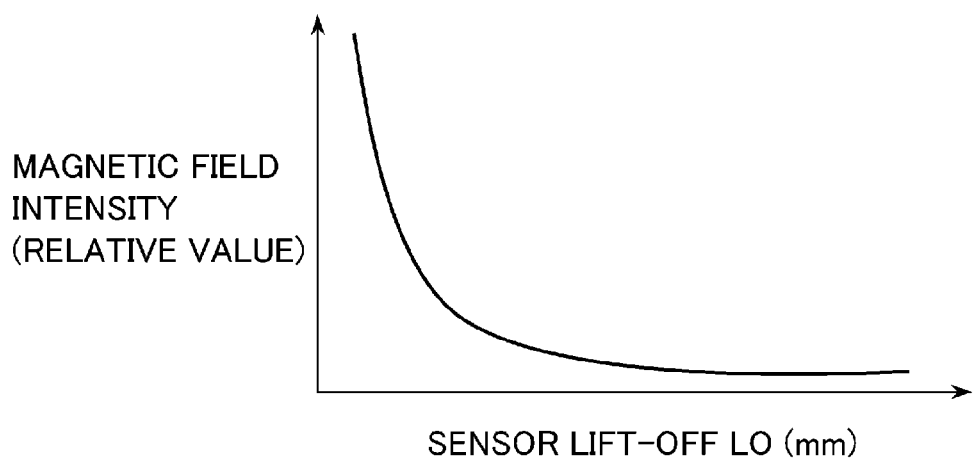

FIGS. 8A and 8B are a schematic diagram and a graph for explaining the magnetic field intensity when the lift-off LO has occurred between the thin film sensor and the inspection object.

FIG. 8A shows a state in which the lower end (i.e., the thin film sensor (see the magnetophotonic crystal film 3 of FIG. 2)) of the inspection probe 11 is not in contact with the inspection object 4, that is, the lift-off LO has occurred. With the increase in the lift-off LO, the distance of the leakage magnetic field from the position of leaking out from the inspection object surface to the position of reaching the thin film sensor increases.

FIG. 8B is a graph showing the relationship between the lift-off and attenuation of the magnetic field intensity. The magnetic field intensity is sharply attenuated by the occurrence of the lift-off. This means that even a slight lift-off makes it impossible to acquire the magnetic field inspection images.

Since the thin film sensor according to this embodiment is capable of reducing the lift-off in the normal setting, the magnetic field sensing position can be kept close to the inspection object and the sensitivity of the detection of cracks, etc. can be increased.

Further, the sensor of this embodiment (FIG. 7) does not employ high-reflectivity material (e.g., aluminum) for reflecting light as in the conventional example of FIG. 6. The micro-cavity structure formed by the dielectric mirrors 31 and 32 in this embodiment (FIG. 8) has the property of transmitting (allowing through) or reflecting light of a particular wavelength. Thus, the reflective plate formed of high-reflectivity material (e.g., aluminum) can be made unnecessary by determining a light wavelength corresponding to the polarization angle rotation in the magnetic layer 33 and designing the dielectric mirrors 31 and 32 so that light of the determined wavelength is reflected.

Since this measurement method uses a magnetic field, if the magnetic field includes an AC magnetic field or undergoes a change at the time of detecting a crack, eddy current occurs in the aluminum plate and that makes the precise measurement difficult. In contrast, the sensor of this embodiment, not employing aluminum, is capable of measuring the magnetic field distribution more precisely compared to the thin film sensor configured as FIG. 6.

Next, inspection images acquired by the inspection device of this embodiment will be explained below referring to FIGS. 9A-12. FIGS. 9A-12 are schematic diagrams for explaining the inspection images acquired by the inspection device according to the embodiment of the present invention.

Figure 9A:
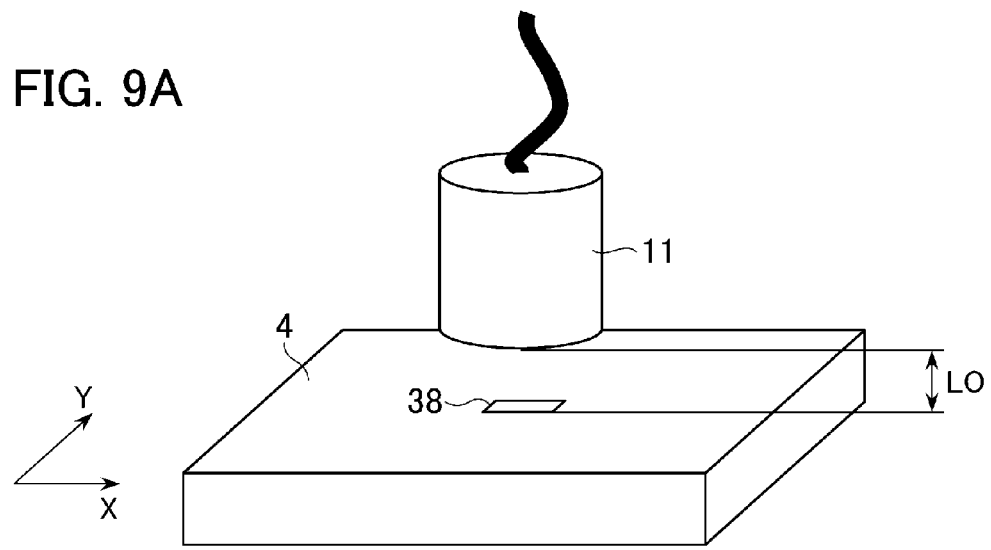
FIGS. 9A-9C are schematic diagrams for explaining inspection images acquired by the inspection device according to the embodiment of the present invention.
Figure 9B:
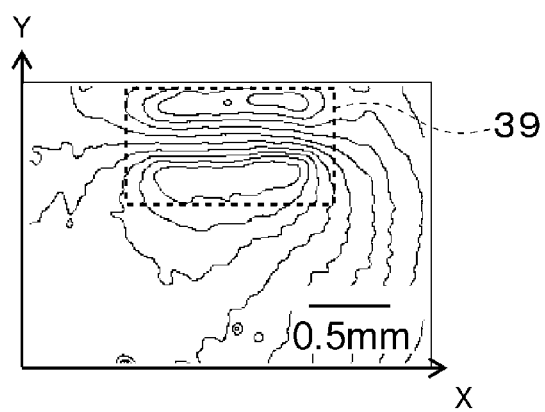
Figure 9C:
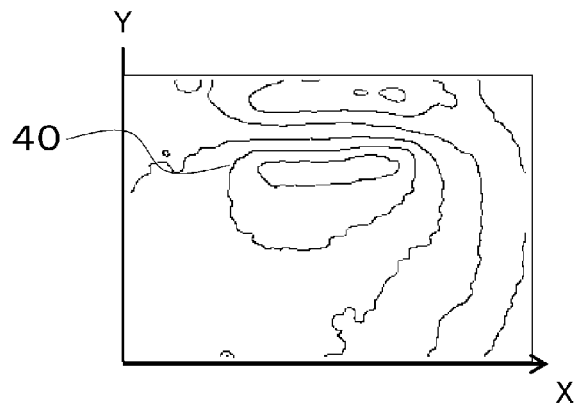

FIGS. 9A-9C are schematic diagrams for explaining magnetic field inspection images acquired by forming a slit flaw 38 on a metal flat plate and capturing an image of the slit flaw 38 with the inspection probe of this embodiment. As shown in FIG. 9A, the slit flaw 38 has been formed on the surface of the inspection object 4. The flaw 38 was formed in a rectangular shape for easiness of comparison between the actual flaw shape and the flaw shape in the inspection image.

FIG. 9B shows a magnetic field inspection image acquired when the thin film sensor was in contact with the inspection object surface, that is, when the lift-off LO was 0. FIG. 9C shows a magnetic field inspection image acquired when the lift-off occurred to the thin film sensor, that is, when the lift-off LO was greater than 0.

Inside the dashed line frame 39 shown in FIG. 9B, the magnetic field leaking out from a crack formed high black/white contrast and was captured as the magnetic field inspection image. In contrast, the example of FIG. 9C has blurring 40 of the detected magnetic field distribution due to the occurrence of the lift-off.

In such cases, it is possible in ordinary magnetic field inspection to make compensation by use of the correction unit of the image generation unit 9 shown in FIG. 1, by previously acquiring data regarding the properties of the lift-off and calculating a coefficient (for compensating for the drop in the sensitivity) for the obtained signal. For this compensation, measurement of the lift-off is necessary. The measured lift-off is stored in a storage unit of the image generation unit 9 shown in FIG. 1 as the compensation coefficient.

However, for the lift-off occurring directly under a surface like the surface of the thin film sensor, the compensation can be made only by removing the probe (in order to directly measure the lift-off), measuring the amount (value) of the lift-off, and making the compensation by using the measured value.

In contrast, the magnetophotonic crystal film employed in this embodiment changes its transmission/reflection property depending on the wavelength of the light; there exists light of a certain wavelength capable of passing through the thin film sensor. Further, since the reflective plate of high reflectivity (e.g., aluminum plate) is not used in the thin film sensor of this embodiment, an image after the passage through the thin film sensor can be acquired as long as there exists light of a certain wavelength capable of passing through the thin film sensor.

Figure 10A:
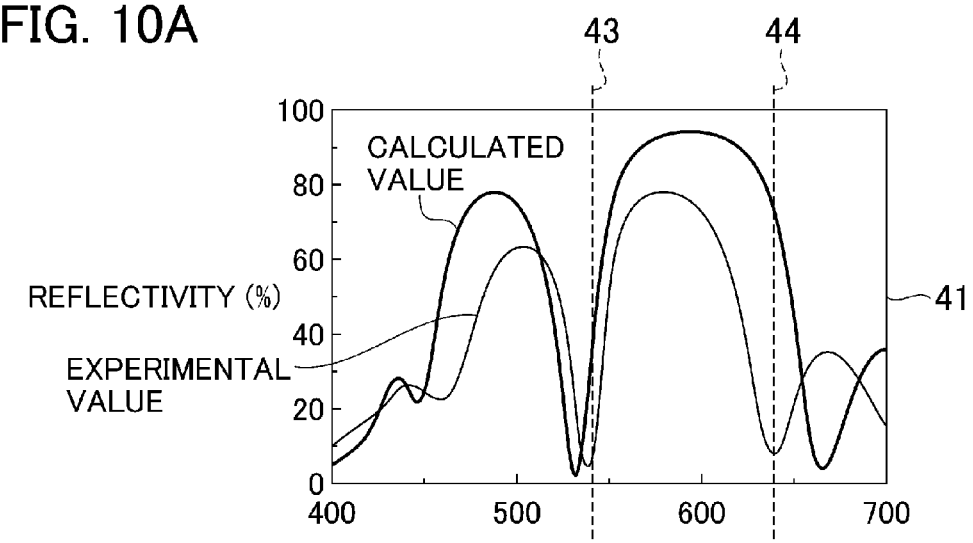
FIG. 10A is a graph obtained by plotting the result of measurement of reflectivity of the magnetophotonic crystal film of this embodiment for various light wavelengths.
Figure 10B:
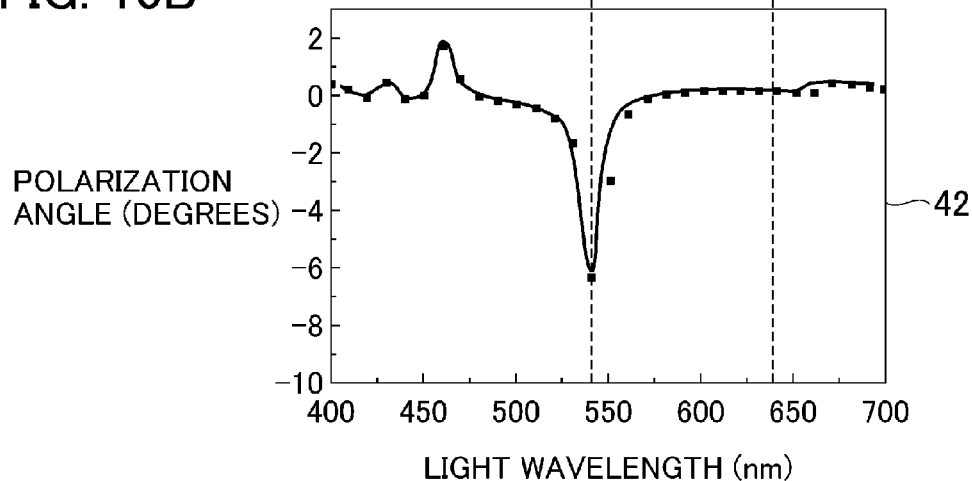
FIG. 10B is a graph obtained by plotting the result of measurement of polarization angle rotation (representing the sensitivity to the magnetic field) in the magnetophotonic crystal film of this embodiment for various light wavelengths.

FIG. 10A is a graph obtained by plotting the result of measurement of the reflectivity 41 of the magnetophotonic crystal film of this embodiment for various light wavelengths. FIG. 10B is a graph obtained by plotting the result of measurement of the polarization angle rotation 42 (representing the sensitivity to the magnetic field) in the magnetophotonic crystal film of this embodiment for various light wavelengths.

In this example, the reflectivity 41 becomes substantially 0% at the wavelength 43 (540 nm) at which the polarization angle rotation 42 (absolute value) hits the maximum. This means that 540 nm is a wavelength of light that is not transmitted (allowed through), the optical path length is increased by the localization of the light in the magnetic layer, and information on a magnetic field distribution having a great polarization plane rotation angle is acquired.

On the other hand, at the wavelength 44 (in the vicinity of 630 nm) at which the magnetic field polarization angle rotation 42 is close to 0 degrees, the reflectivity is low and the transmittance is high. This indicates that the an optical image after the passage through the thin film sensor can be captured and displayed with substantially no image disturbance with respect to the magnetic field.

To sum up, both the magnetic field inspection image and the optical inspection image can be acquired by using light of two or more different wavelengths.

Figure 11:
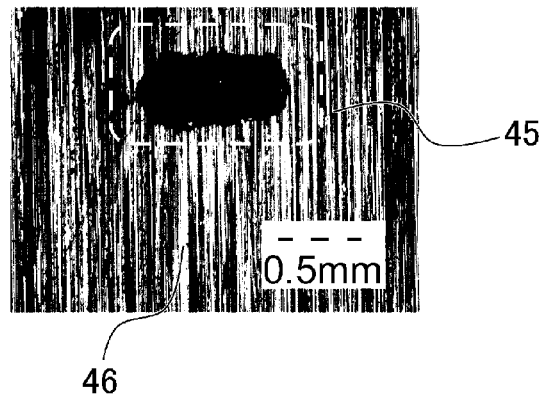
FIG. 11 is a schematic diagram showing an optical inspection image captured by using light of the wavelength (630 nm) shown in FIGS. 10A and 10B.

FIG. 11 shows an optical inspection image captured by using light of the wavelength 44 (630 nm) shown in FIGS. 10A and 10B. Even though this image was captured via the magnetophotonic crystal film, the surface of the inspection object is imaged successfully and the opening of the slit defect (in the broken line frame 45 in FIG. 11) is visually recognizable. It is also possible to check the status of the inspection object surface, clearly capture images of polishing scratches 46 on the inspection object surface, and conduct the visual checks without the need of removing the probe.

Since it is possible, in the case of the optical inspection image, to acquire optical images of the surface of the inspection object situated beyond the thin film sensor, distance measurement at each position in the optical inspection image is possible according to a principle like that of the laser displacement sensor. Since the distance between the thin film sensor and the inspection object surface is measurable, it is possible to compensate for the lift-off error (error corresponding to the lift-off) in the magnetic field inspection image by using a previously measured property of the magnetic field sensitivity attenuation due to the lift-off.

FIG. 12 is a table showing an example of the result of the calculation of the compensation coefficients. An optical image was obtained by changing a wavelength of a light at the position of the magnetic field inspection image of FIG. 9C having the lift-off. The compensation coefficients were determined based on data of previously measured magnetic field sensitivity varying depending on the lift-off (e.g., the data shown in FIG. 8B). The determined compensation coefficients were mapped as shown in FIG. 12. The obtained compensation coefficients are stored in the storage unit of the image generation unit 9 shown in FIG. 1. The correction unit of the image generation unit 9 shown in FIG. 1 is capable of acquiring a magnetic field inspection image with entire-image correction (compensation), by performing the compensation on the pixel points of the (original) magnetic field inspection image by using the compensation coefficients for the pixel values.

The image acquired as above is a magnetic field inspection image in which the correction (compensation) has been made by evaluating the lift-off at each pixel point based on the data of the optical image. With such an image correction method, blurred images can be made clearer.

The compensation coefficient distribution shown in FIG. 12 may also be displayed as the lift-off. Displaying such information on a display device makes it possible to monitor the measured conditions. When the lift-off is excessive, a warning may be issued so as to prompt the inspector to reexamine the probe setting conditions.

According to the embodiment described above, the sensor lift-off can be reduced by the magneto-optical measurement method employing a magnetophotonic crystal film. Therefore, the magnetic field detection sensitivity is increased and that leads to improvement in the accuracy of the magnetic field inspection.

Further, by using light of multiple wavelengths, both the magnetic inspection and the optical inspection can be conducted without the need of physically moving the probe and the magnetic inspection data can be corrected based on the optical inspection data. Therefore, the accuracy of the inspection can be improved.

Furthermore, even when the magnetic field detection sensitivity drops due to the occurrence of the lift-off (increase in the distance between the sensor and the inspection object), it is possible to compensate for the drop in the magnetic field detection sensitivity by measuring the amount of the lift-off.

Second Embodiment

Next, an inspection device and an inspection method in accordance with a second embodiment of the present invention will be described below referring to FIG. 13. FIG. 13 is a block diagram showing the overall configuration of the inspection device according to the second embodiment of the present invention. In FIG. 13, reference characters identical with those in FIG. 1 represent components identical with those in FIG. 1.

While the inspection device of this embodiment has substantially the same configuration as the device of FIG. 1, an autofocus lens 101 is employed in this embodiment for the following reason: Since the distance between the photoreceptor device 25 (e.g., camera) and the focal point is changed for the acquisition of the magnetic field inspection image and the optical inspection image, it has been necessary to adjust the lens or to prepare multiple lenses suitable for the different focal lengths. By employing the autofocus lens 101 for the lens unit of the selection unit 6A presiding over this function, the focusing can be carried out in conjunction with the change of the wavelength.

Also in this embodiment, the sensor lift-off can be reduced by the magneto-optical measurement method employing a magnetophotonic crystal film. Therefore, the magnetic field detection sensitivity is increased and that leads to improvement in the accuracy of the magnetic field inspection.

By using light of multiple wavelengths, both the magnetic inspection and the optical inspection can be conducted without the need of physically moving the probe and the magnetic inspection data can be corrected based on the optical inspection data. Therefore, the accuracy of the inspection can be improved.

Even when the magnetic field detection sensitivity drops due to the occurrence of the lift-off (increase in the distance between the sensor and the inspection object), it is possible to compensate for the drop in the magnetic field detection sensitivity by measuring the amount of the lift-off.

Figure 3:
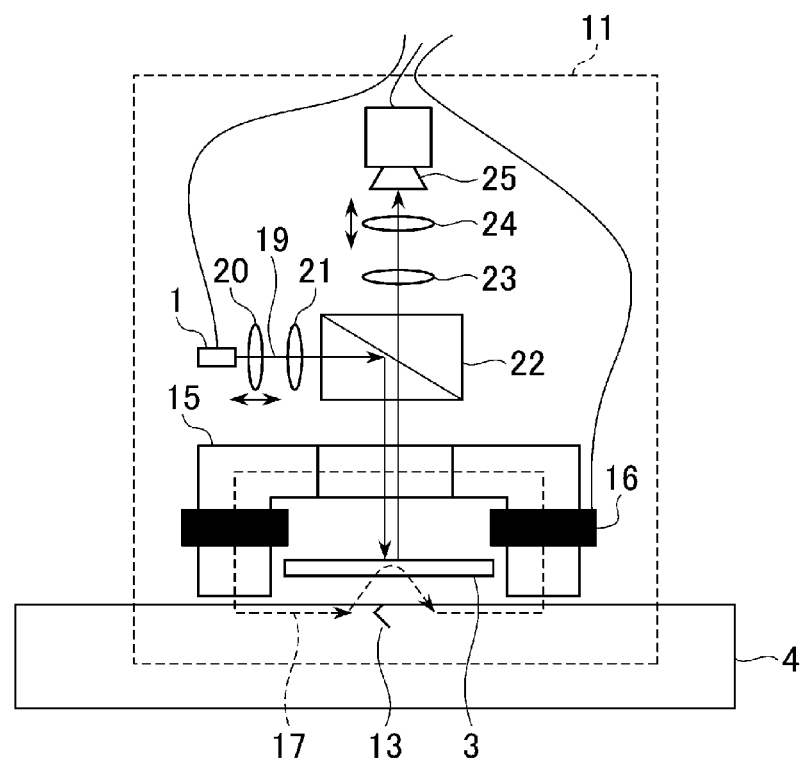
FIG. 3 is a detailed configuration diagram of a principal part of the inspection device according to the first embodiment of the present invention.

It is also possible to use an optical system employing optical fibers instead of the optical system shown in FIG. 3. In this case, the light of the first wavelength emitted from the light-emitting unit enters an optical fiber, passes through the optical fiber, and irradiates the (thin-film shaped) magnetophotonic crystal film (arranged immediately above the inspection object surface) via a circulator. The light of the second wavelength emitted from the light-emitting unit enters an optical fiber, passes through the optical fiber, and irradiates the inspection object surface via a circulator. The irradiation unit is configured as above.

By using the light of the first wavelength applied by the irradiation unit to the magnetophotonic crystal film, the magnetic field inspection information is received via an optical fiber and a lens. By using the light of the second wavelength applied by the irradiation unit to the inspection object surface, the inspection object surface information is received via an optical fiber and a lens. The selection unit is configured as above.

Third Embodiment

Next, the configuration and operation of an inspection device in accordance with a third embodiment of the present invention will be described below referring to FIGS. 14A-16C.

FIGS. 14A-16C illustrate an embodiment in which an optical system employing an optical fiber is used.

Figure 14A:
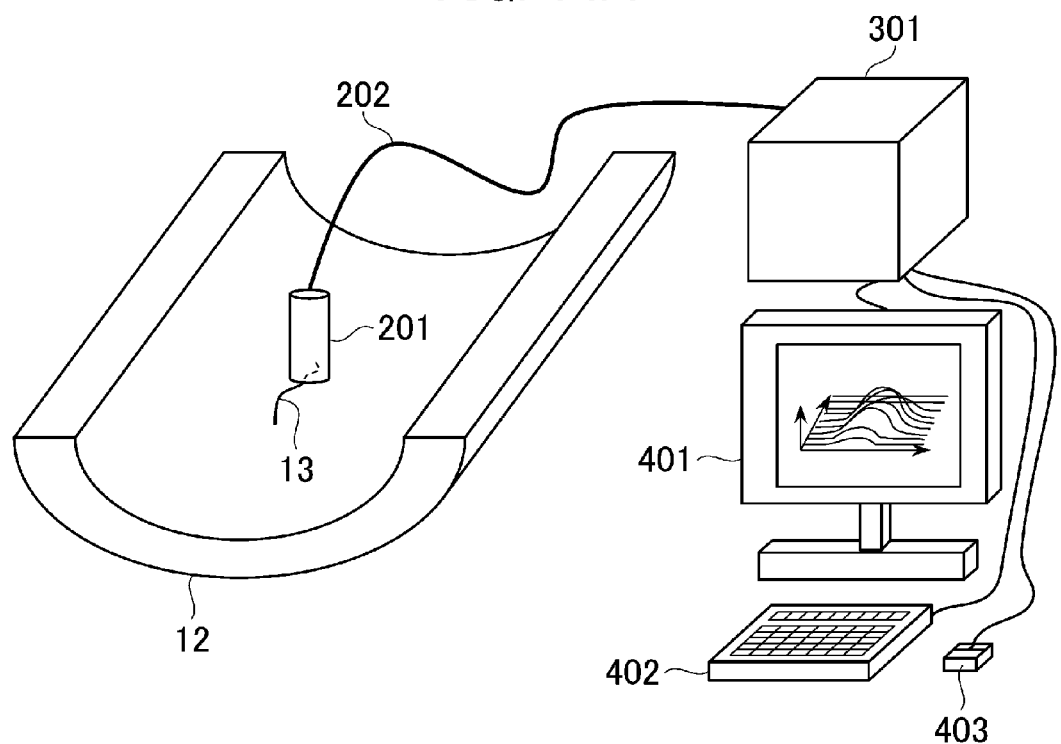
FIG. 14A is a perspective view showing the overall configuration of an inspection device according to a third embodiment of the present invention.
Figure 14B:
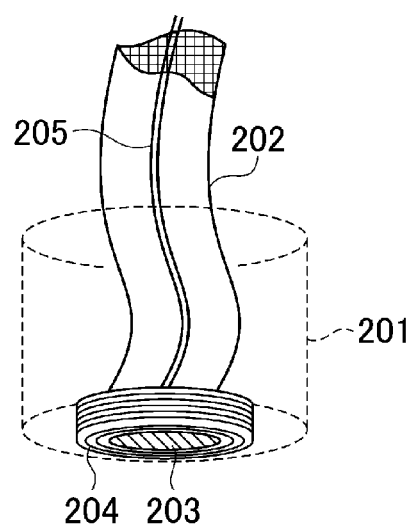
FIG. 14B is a schematic diagram showing an example of the internal structure of a probe of the inspection device shown in FIG. 14A.

FIGS. 14A and 14B show an example of a measurement scheme of the inspection device employing an optical fiber. As shown in FIG. 14A, a sensor unit of the probe 201 is connected to an inspection device main unit 301 (main unit of the inspection device) via a cable 202 formed of an optical fiber. A monitor 401 for displaying measurement images and input devices to be used for inputting probe control information and for operating the measurement images (e.g., a keyboard 402 and a pointing device 403) are connected to the inspection device main unit 301. This configuration allows the inspector to observe the inspection data acquired according to the present invention.

Since the optical system can be moved freely thanks to the optical fiber, it is possible to stably set the probe 201 at an appropriate position even for narrow parts (where insertion of the probe is difficult) and for flaws 13 of inspection objects 12 having a curved surface.

FIG. 14B illustrates an example of the internal structure of the probe 201. A magnetophotonic crystal film 203 is arranged at the tip end of the optical fiber. A coil 204 for generating the magnetic field is arranged inside the probe. The probe can be downsized by installing the coil 204 by using the optical fiber as the coil axis, for example. The coil 204 is connected to an excitation power supply in the inspection device main unit 301 by lead wires 205 extending from the coil 204 along with the optical fiber.

Figure 15:
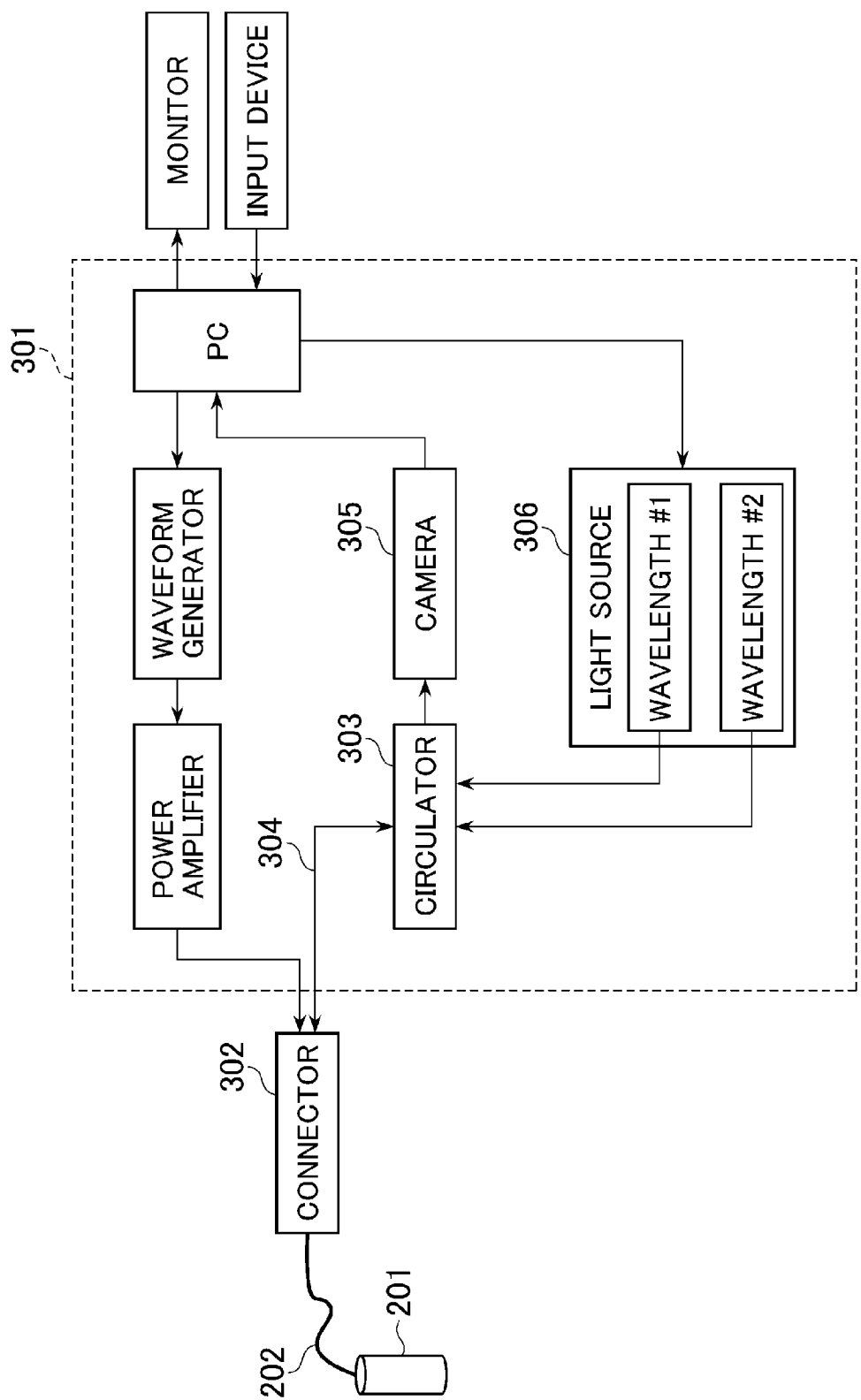
FIG. 15 is a block diagram showing the configuration of the main unit of the inspection device shown in FIG. 14A.

FIG. 15 shows the configuration of the inspection device main unit 301. The cable 202 formed of the optical fiber, the coil lead wires, etc. is connected to the inspection device main unit 301 via a connector 302.

Connected to the coil lead wires is a power amplifier. The excitation current control is performed by a waveform generator and a PC. The optical fiber connected from the outside of the inspection device (inspection device main unit 301) is connected to an optical transmission line 304 which is connected to a circulator 303 inside the inspection device. The optical transmission line 304 transmits the input/output light to/from the probe 201 by use of an optical fiber and/or a space. The circulator 303 is provided for the purpose of changing the input/output directions of the light to/from a light source 306 and a camera 305. The light source 306, which serves as a control unit for changing the wavelength of the output light according to commands from the PC, is capable of changing the wavelength of the light inputted/outputted to/from the probe 201.

Figure 16A:
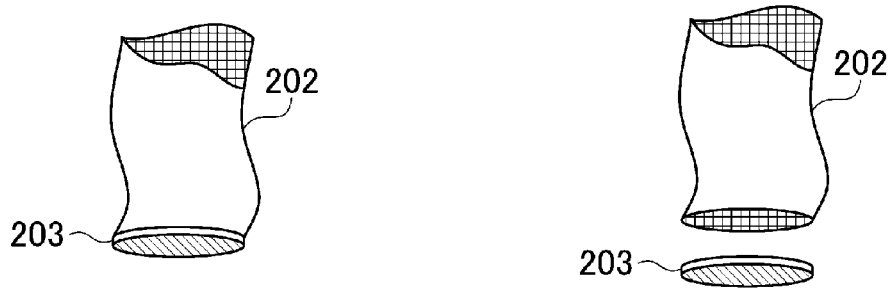
FIGS. 16A-16C are schematic diagrams showing examples of the arrangement of an optical fiber and the magnetophotonic crystal film inside the probe.
Figure 16B:
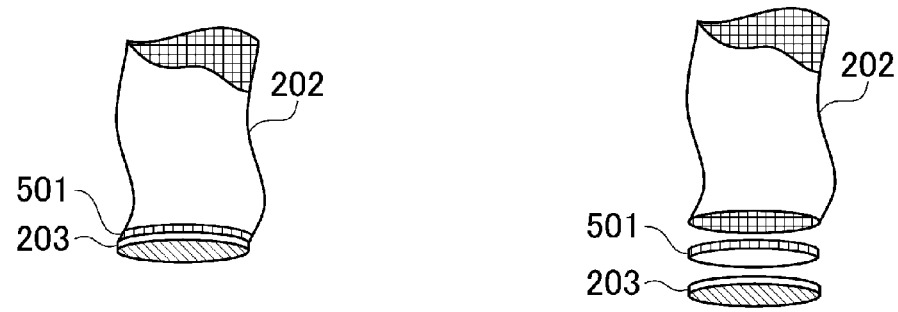
Figure 16C:
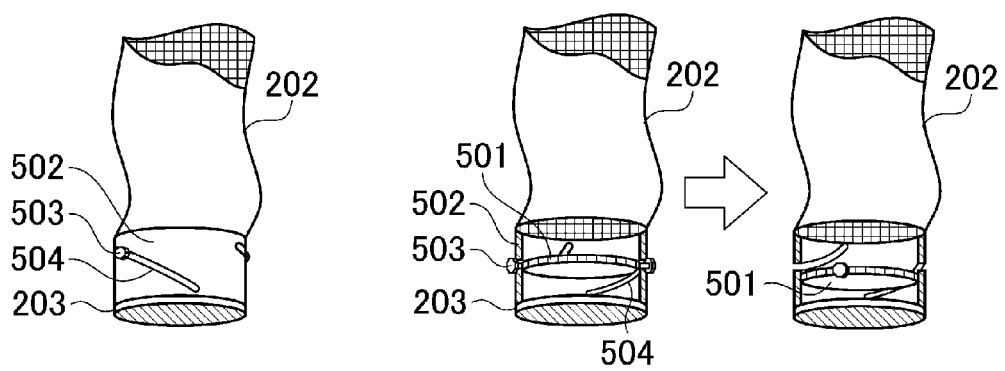

FIGS. 16A-16C are schematic diagrams showing examples of the arrangement of the optical fiber 202 and the magnetophotonic crystal film 203 inside the probe 201. The left-hand side and the right-hand side of each figure indicate the final structure and exploded structure, respectively.

A fiber scope formed by bundling a lot of optical fibers is usable as a tool for acquiring images by use of optical fibers. By equipping the fiber scope 202 with the magnetophotonic crystal film 203 as shown in FIG. 16A, the magnetic field inspection image and the optical inspection image can be acquired by use of light of two or more different wavelengths according to the present invention.

In cases where focus adjustment of a lens or the like is necessary for clearly capturing the magnetic field inspection image and the optical inspection image, it is also possible to insert a lens 501 between the optical fiber 202 and the magnetophotonic crystal film 203 as shown in FIG. 16B.

In cases where the optical inspection image should be captured clearly even with great variations in the distance between the probe and the inspection object, it is possible to provide the probe with a function of guiding the lens 501 as shown in FIG. 16C so that the position of the lens 501 inserted between the optical fiber 202 and the magnetophotonic crystal film 203 can be changed.

FIG. 16C shows an example of the probe structure for changing the position of the lens 501. In order to secure a space between the fiber scope 202 and the magnetophotonic crystal film 203, a hollow frame 502 connecting the fiber scope 202 and the magnetophotonic crystal film 203 is provided. The internal diameter of the frame 502 is substantially the same as the external diameter of the lens 501, and thus the lens 501 can be fit within the areas of the fiber scope 202 and the magnetophotonic crystal film 203. Projections 503 are formed on the outer circumference of the lens 501. Further, the frame 502 is provided with slits 504 for serving as guides for the projections 503. The position of the lens 501 can be changed by using the projections 503 engaged with the slits 504. In the example of FIG. 16C, each slit 504 is formed obliquely to the axial direction of the frame 502. Thus, by sliding the projection(s) 503 in the circumferential direction of the frame 502, it is possible to move the lens 501 in the axial direction of the frame 502, change the focal distance to the inspection object, and adjust the focal point also to the magnetophotonic crystal film 203.

With the configuration described above, the magnetic field inspection image and the optical inspection image can be acquired by use of an optical fiber or a fiber scope and light of two or more different wavelengths according to the present invention.

The following configurations are possible as modes of implementation of the present invention:

(Implementation 1)

The inspection device for evaluating characteristic changes in an inspection object such as flaws and material property changes by using magnetism, wherein the inspection device employs a magnetophotonic crystal film.

(Implementation 2)

The inspection device according to implementation 1, wherein:

the magnetophotonic crystal film is a film-shaped magnetic field detection element arranged immediately above an inspection object surface of the inspection object in order to detect a magnetic field generated by an excitation unit, and the inspection device comprises:

a light-emitting unit which emits light of a first wavelength for acquiring magnetic field inspection information and a second wavelength for acquiring inspection object surface information;

an irradiation unit which irradiates the inspection object with the light from the light-emitting unit;

a selection unit which selects information from the inspection object and information from the magnetophotonic crystal film acquired by the light irradiation by the irradiation unit as the inspection object surface information and the magnetic field inspection information;

an image generation unit which generates image data based on the magnetic field inspection information acquired with the first wavelength and the inspection object surface information acquired with the second wavelength selected by the selection unit; and a display unit which displays the image data generated by the image generation unit.

(Implementation 3)

The inspection device according to implementation 2, wherein the irradiation unit is configured so that:

the light of the first wavelength emitted from the light-emitting unit enters an optical fiber and irradiates via a circulator the magnetophotonic crystal film arranged immediately above the inspection object surface, and the light of the second wavelength emitted from the light-emitting unit enters an optical fiber and irradiates the inspection object surface via a circulator.

(Implementation 4)

The inspection device according to implementation 2, wherein:

the selection unit receives reflected light from the magnetophotonic crystal film being irradiated with the light of the first wavelength by the irradiation unit as the magnetic field inspection information via a half mirror and a lens, and the selection unit receives reflected light from the inspection object surface being irradiated with the light of the second wavelength by the irradiation unit as the inspection object surface information via a half mirror and a lens.

(Implementation 5)

The inspection device according to implementation 2, wherein:

the selection unit receives reflected light from the magnetophotonic crystal film being irradiated with the light of the first wavelength by the irradiation unit as the magnetic field inspection information via an optical fiber and a lens, and the selection unit receives reflected light from the inspection object surface being irradiated with the light of the second wavelength by the irradiation unit as the inspection object surface information via an optical fiber and a lens.

(Implementation 6)

The inspection device according to implementation 4 or 5, wherein:

an autofocus lens is used as the lens, and the selection unit adjusts the focal point of the light of the first wavelength irradiating the magnetophotonic crystal film and the focal point of the light of the second wavelength irradiating the inspection object surface.

What is claimed is:

1. An inspection device for evaluating characteristic changes in an inspection object such as flaws and material property changes by using magnetism, the inspection device comprising:

a magnetophotonic crystal film, wherein the magnetic photonic magnetophotonic crystal film is a film-shaped magnetic field detection element arranged immediately above an inspection object surface of the inspection object in order to detect a magnetic field generated by an excitation unit, and the inspection device comprises:

a light-emitting unit configured to emit light of a first wavelength that acquires magnetic field inspection information by reflecting light inside of the magnetophotonic crystal and a second wavelength that acquires inspection object surface information by passing light through the magnetophotonic crystal, wherein said magnetophotonic crystal film is sandwiched between two dielectric mirrors such that multiple reflections are produced between the dielectric mirrors;

a selection unit which selects information from the inspection object and information from the magnetophotonic crystal film acquired by the light irradiation by the irradiation unit as the inspection object surface information and the magnetic field inspection information;

an image generation unit which generates image data based on the magnetic field inspection information acquired with the first wavelength and the inspection object surface information acquired with the second wavelength selected by the selection unit; and a display unit which displays the image data generated by the image generation unit.

2. The inspection device according to claim 1, wherein:
the light of the first wavelength emitted by the light-emitting unit is light that is high in the ratio of the change in the polarization angle with respect to the magnetic field intensity in the magnetophotonic crystal film, and
the light of the second wavelength emitted by the light-emitting unit is light that is low in the ratio of the change in the polarization angle with respect to the magnetic field intensity in the magnetophotonic crystal film and is high in the transmittance.

3. The inspection device according to claim 1, wherein:
the irradiation unit applies the light of the first wavelength emitted by the light-emitting unit to the magnetophotonic crystal film arranged immediately above the inspection object surface via a half mirror, and
the irradiation unit applies the light of the second wavelength emitted by the light-emitting unit to the inspection object surface via the half mirror.

4. The inspection device according to claim 1, wherein the image generation unit includes a correction unit which corrects data of the magnetic field inspection information acquired with the light of the first wavelength based on the inspection object surface information acquired with the light of the second wavelength.

5. The inspection device according to claim 4, wherein:
the correction unit prestores sensitivity data corresponding to the distance between the inspection object surface and the magnetophotonic crystal film, and
the correction unit measures the distance between the inspection object surface and the magnetophotonic crystal film based on the inspection object surface information acquired with the light of the second wavelength and corrects the data of the magnetic field inspection information according to the measured distance.

6. The inspection device according to claim 1, wherein the display unit simultaneously displays an image of the magnetic field inspection information acquired with the light of the first wavelength and an image of the inspection object surface information acquired with the light of the second wavelength.

7. The inspection device according to claim 1, wherein the display unit simultaneously displays an image of the magnetic field inspection information acquired with the light of the first wavelength and data of the distance between the inspection object surface and the magnetophotonic crystal film measured based on the inspection object surface information acquired with the light of the second wavelength.

8. An inspection method for evaluating characteristic changes in an inspection object such as flaws and material property changes,
wherein the characteristic changes such as flaws and material property changes are detected by a magnetic field inspection while also detecting flaws on the inspection object surface by an optical inspection by performing the following steps:

irradiating a magnetophotonic crystal film with light of a first wavelength that acquires magnetic field inspection information emitted from a light-emitting unit by reflecting light inside of the magnetophotonic crystal, wherein said magnetophotonic crystal film is sandwiched between two dielectric mirrors;

irradiating the inspection object with light of a second wavelength that acquires inspection object surface information emitted from the light-emitting unit passing light through the magnetophotonic crystal, such that multiple reflections are produced between the dielectric mirrors;

generating image data based on the magnetic field inspection information acquired from the magnetophotonic crystal film and the inspection object surface information acquired from the inspection object; and displaying the generated image data.

9. The inspection method according to claim 8, comprising the steps of:
storing sensitivity data corresponding to the distance between the inspection object surface and the magnetic photonic crystal film;
measuring the distance between the inspection object surface and the magnetophotonic crystal film based on the inspection object surface information acquired with the light of the second wavelength; and
generating the image data by correcting the data of the magnetic field inspection information by using the measured distance and the sensitivity data.

10. The inspection device according to claim 1, wherein the magnetophotonic crystal film is constituted by a magnetic layer that is sandwiched between, and that is in direct contact with, a first laminated dielectric mirror and a second laminated dielectric mirror that selectively allow some electromagnetic waves to pass therethrough and that selectively reflect some other electromagnetic waves, the first laminated dielectric mirror having a tantalum pentoxide layer in direct contact with an oxide silicon layer, and the second laminated dielectric mirror having at least one oxide silicon layer in direct contact with at least two tantalum pentoxide layers.

11. The inspection method according to claim 8, wherein the magnetophotonic crystal film is constituted by a magnetic layer that is sandwiched between, and that is in direct contact with, a first laminated dielectric mirror and a second laminated dielectric mirror that selectively allow some electromagnetic waves to pass therethrough and that selectively reflect some other electromagnetic waves, the first laminated dielectric mirror having a tantalum pentoxide layer in direct contact with an oxide silicon layer, and the second laminated dielectric mirror having at least one oxide silicon layer in direct contact with at least two tantalum pentoxide layers.

12. An inspection device for evaluating characteristic changes in an inspection object such as flaws and material property changes by using magnetism, comprising:
a magnetophotonic crystal film having a magnetic layer that is sandwiched between, and that is in direct contact with, a first laminated dielectric mirror and a second laminated dielectric mirror that selectively allow some electromagnetic waves to pass therethrough and that selectively reflect some other electromagnetic waves, the first laminated dielectric mirror having a tantalum pentoxide layer in direct contact with an oxide silicon layer, and the second laminated dielectric mirror having at least one oxide silicon layer in direct contact with at least two tantalum pentoxide layers.

* * * * *